United States Patent [19]

Morgan et al.

[11] 4,066,404

[45] Jan. 3, 1978

[54] DETERMINATION OF DEUTERIUM CONCENTRATION IN WATER

[75] Inventors: Thomas D. Morgan; Robert B. Regier, both of Bartlesville, Okla.

[73] Assignee: Phillips Petroleum Company, Bartlesville, Okla.

[21] Appl. No.: 711,032

[22] Filed: Aug. 2, 1976

[51] Int. Cl.² .................. B01J 25/02; G01N 33/18; G01N 33/24
[52] U.S. Cl. ............................ 23/230 EP; 23/230 R
[58] Field of Search ............... 23/230 EP, 230 R; 252/477 Q

[56] References Cited

PUBLICATIONS

Fischer et al., Anal. Chem. 20, 571 (1948).
Orchin et al., Anal. Chem. 21, 1072 (1949).
Alfin-Slater et al., Anal. Chem. 22, 421 (1950).
Friedman et al., Anal. Chem. 24, 876 (1952).

Primary Examiner—Robert M. Reese

[57] ABSTRACT

Water samples having a predetermined concentration of deuterium are equilibrated with a hydrogen containing reagent at such conditions as to allow migration of hydrogen and deuterium ions between the reagent and water. The reagent is then analyzed to determine the isotope ratio of molecules containing deuterium to those containing hydrogen. From the data, a correlation between isotope ratio and the concentration of deuterium in water is established. The sample of water having an unknown concentration of deuterium is then equilibrated under the same conditions with the same reagent. The equilibrated reagent is analyzed to determine mass isotope ratio which is converted to deuterium concentration in water using previously established correlation. Deuterium concentration in water is then used for obtaining geothermal data.

5 Claims, 1 Drawing Figure

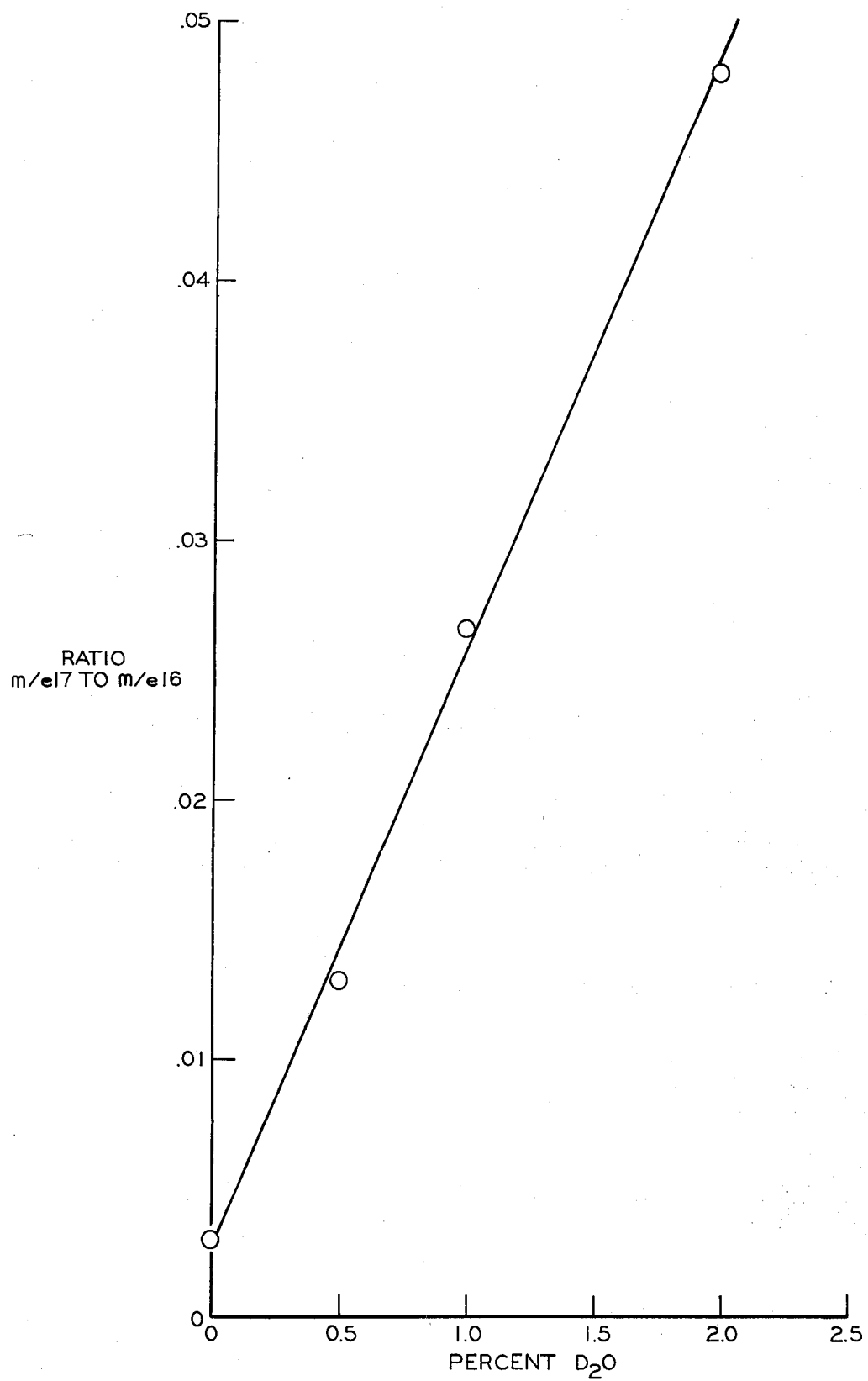

DETERMINATION OF DEUTERIUM CONCENTRATION IN WATER

BACKGROUND OF THE INVENTION

This invention relates to a method for determining the concentration of deuterium in water. In particular, it relates to the use of this method for estimating the highest temperature that water has attained.

It is helpful in geothermal exploration to determine the highest temperature that a given body of water was subjected to. This temperature affects the deuterium concentration in water; consequently, geothermal data can be obtained by determining deuterium concentration of water which is being investigated.

To measure deuterium concentration by a traditional method, hot uranium or zinc is reacted with water causing hydrogen and deuterium ions to be converted to free elements. The hydrogen-deuterium gas which evolves in the reaction is then analyzed in an isotope ratio mass spectrometer. The first step of the conventional process is expensive, difficult, cumbersome and timeconsuming; the second step lacks in reliability and accuracy because $H_3^+$ ions, forming in the source, having mass approximately the same as $HD^+$ ions (one of the principal ions examined by isotope ratio mass spectrometry) interfere with the analysis.

Another approach was to convert a water sample having unknown $D_2O$ concentration to HCl by reaction with $SiCl_4$. The HCl was then passed to a mass spectrometer and the ratio of peaks at mass 38 ($H^1Cl^{37}$) and mass 39 ($H^2Cl^{37}$) was determined. Substantial difficulties were encountered, however, in the analysis by mass spectrometer as hydrocarbon impurities contained in water gave a large peak at mass 39.

The present invention obviates difficulties encountered in the process for determining deuterium concentration in water.

Thus, one object of the present invention is to provide a process for determination whether a given sample of water emerged from a geothermal reservoir, i.e., was at one time heated to a high temperature by naturally occurring hot formations near the surface.

Another object of the invention is to provide a process for determining deuterium concentration in water, which eliminates the necessity for complicated extraction of free hydrogen and deuterium from water.

Still another object of the invention is to provide a process for determining deuterium concentration in water, accuracy of which is not affected by the formation of $H_3^+$ ions during isotope ratio mass spectrometry.

A still further object of the invention is to provide a process for determining deuterium concentration in water, which is rapid, efficient, accurate and inexpensive to perform.

Still another object of the invention is to provide a process for determining deuterium concentration in water, which eliminates the need for sophisticated equipment, intricate operating procedures, and large samples.

Other objects of the invention will become apparent to those skilled in the art upon studying the specification and the appended claims.

SUMMARY OF THE INVENTION

One aspect of the invention is to equilibrate water sample of unknown deuterium concentration with a hydrogen containing reagent at such conditions as to produce an exchange of hydrogen between the reagent and water so that deuterium ions present in water distribute themselves between water and the reagent. The reagent to which deuterium ions migrate must be a gas at the conditions present during analysis. The mass isotope ratio of equilibrated reagent molecules containing deuterium and those containing hydrogen is then determined. This ratio is converted to deuterium concentration in water using the correlation obtained by equilibrating samples of water containing known and varied amounts of deuterium with the same reagent under the same conditions for the same period of time and analyzing for mass isotope ratios.

Another aspect of the invention is to equilibrate water and methane in the presence of Raney nickel catalyst so that some of the deuterium ions originally present in water migrate into methane molecules and some hydrogen molecules migrate into water from methane. The methane gas is then introduced into isotope mass spectrometer and the mass ratio of methane molecules containing deuterium to those which do not contain deuterium is determined. This ratio is then converted to deuterium concentration in water using a correlation obtained by equilibration with the same quantities of reagents under the same conditions and for the same period of time with a number of water samples having known and varied concentrations of deuterium.

Other aspects of the invention will become apparent to those skilled in the art upon studying this disclosure.

BRIEF DESCRIPTION OF THE FIGURE

The FIGURE depicts the correlation m/e 17 /m/e 16 and deuterium concentration in water obtained in Example I.

DETAILED DESCRIPTION OF THE INVENTION

In accordance with this invention, a water sample having unknown $D_2O$ concentration is equilibrated with a hydrogen containing reagent to permit migration of deuterium from water to the reagent where these replace hydrogen. The reagent is then analyzed in a suitable apparatus to determine the mass ratio of molecules containing deuterium to those containing hydrogen. This ratio is converted to deuterium concentration in water using a correlation obtained consecutively by equilibrating water samples of known and varied deuterium concentration with the same reagent under exactly the same conditions.

If a correlation is utilized for obtaining $D_2O$ concentration, small concentration of deuterium (in comparison to the deuterium concentration in water) can be present in the reagent; however, it is preferable to use reagents which contain substantially no deuterium. The reagent suitable for the use with this invention can be any hydrogen containing compound in which hydrogen constitutes the reactive site. Among preferred reagents are hydrocarbons, especially saturated hydrocarbons such as methane. Since the reagent analyzed in the mass spectrometer must be in gaseous state during analysis, if mass spectrometry is used to determine isotope mass ratio usually a reagent which is in gaseous state at room temperature is selected. Although not absolutely necessary, it is preferable in practice to choose such reagents and such reaction conditions that all compounds in the reaction zone are relatively inert, non-corrosive, non-lethal and do not form explosive mixtures. Preferred reagents include hydrocarbons such as methane, ethylene, acetylene and propylene especially saturated hydrocarbons. It is also preferable to select reagents and conditions which result in generation of molecules (isotopic ratio of which is subsequently determined) molecular weights of which is significantly different from those of molecules commonly found in or in the vicinity of the analyzer used to determine the isotope ratio and significantly different from the molecular weight of impurities contained in water. For example, if ethane is equilibrated with water to produce ethane containing hydrogen and deuterium ions originally present in water, and equilibrated ethane is analyzed to determine the isotope ratio of ethane having molecular weight of 28 to ethane have molecular weight of 29, nitrogen having molecular weight of 28 interferes with the analysis. It is therefore preferred that a saturated hydrocarbon other than ethane be selected as a reagent for the process of the invention. Excellent results were obtained with methane.

The equilibration must proceed for a sufficient period of time to allow enough deuterium ions originally present in water to migrate to the reagent replacing a hydrogen therein. The relative amounts of water and the reagent can be selected at will, however, it is preferred to use a much higher amount of water than the reagent to maximize the concentration of deuterium in the equilibrated reagent. Usually the weight ratio of water to the reagent is in the range from about 10 to about 1000.

In operation, a water sample having known and varied deuterium concentration is equilibrated with a selected reagent at a predetermined conditions to allow exchange of hydrogen and deuterium between the reagent and water. The equilibration is permitted to proceed for a time period sufficient to generate enough isotope molecules to permit isotope ratio analysis. The water vapor, if any, is removed from the reagent which is then introduced into isotope mass ratio analyzer. One suitable type of an analyzer is an isotope ratio mass spectrometer. Using conventional procedures, isotope ratio is determined. This procedure is repeated using at least one other but preferably several samples of water each having a preselected deuterium concentration different from that of other sample or samples. The same amount of water and the same amount of reagent is used in each one of the runs. The mass isotope ratios are then correlated with the respective deuterium concentrations.

Next, the same amount of water, the deuterium concentrations of which is sought to be determined, is introduced into the equilibration zone with the same amount of the identical reagent as used when making the correlation. It is generally preferred to use the reagent from the same stock as that used for making the correlation, especially if the reagent itself contains deuterium. The reaction is allowed to proceed under exactly the same conditions as those used for obtaining the correlation between deuterium concentration and measured isotope ratio and for the same period of time. The gases are then separated from any water vapor and introduced into the analyzer in which isotope ratio is obtained. This ratio is then substituted into the correlation to obtain the corresponding deuterium concentration of the unknown sample.

One suitable reagent which can be used in this invention is methane. When water and methane are heated in a closed system under selected conditions and in the presence of a suitable catalyst, following reactions occur:

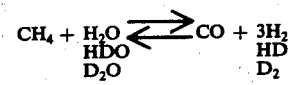

As these reactions approach equilibrium, the hydrogen and deuterium distribute so that the deuterium content of the methane is proportional to the deuterium content of the water. The catalyst that can be used in this reaction include: Raney nickel, disclosed in U.S. Pat. No. 1,628,190; a reduced and stabilized nickel on alumina catalyst; and a nickel-alumina-barium catalyst. It is preferred to use at least 50–500 times as much water as reagent so that when equilibrium is established the products have a high deuterium concentration making the isotope ratio determination easier and more accurate.

The conditions of the reaction should be such as to minimize or eliminate the reaction

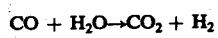

because the formation of hydrogen shifts the equilibrium of the main reactions towards the left. Methane gas is then separated and analyzed by an isotope ratio mass spectrometer to determine m/e 17/m/e 16 ratio. Having obtained that ratio, the values for deuterium content can be read directly from curve correlating m/e 17/m/e 16 ratio to deuterium content in water obtained by reacting samples of water of known deuterium concentration with methane from the same stock. The deuterium content in water is then used together with other data for determining the thermal history of the sampled water.

EXAMPLE I

One gram of Raney nickel catalyst prepared in accordance with U.S. Pat. No. 1,628,190 was placed in a 33 cc. stainless steel sample container. A glass ampule with a break-seal, containing 0.1 ml water was then inserted inside the container. Following this step, the container was evacuated. Next, methane was injected into the container until the pressure reached 200 torr. The break-seal was then broken by shaking the container.

Next, the container was heated in a furnace of 400° C (752° F) at pressures from about 400 to about 600 psi for 1 hour and allowed to cool to room temperature. After cooling, the methane was introduced into the mass spectrometer through a dry ice trap which removed the water vapor. m/e 17 and m/e 16 for methane were then measured using the CEC-21-130 mass spectrometer in a conventional scanning manner.

This procedure was repeated using demineralized water containing from zero to 2.0 percent deuterium. The results are correlated in the figure.

This run indicates that when water containing hydrogen and deuterium ions is equilibrated with methane over Raney nickel catalyst, the deuterium ions distribute in such a manner that the m/e 17/m/e 16 ratio in methane is proportional to the hydrogen to deuterium ratio in water. The levels of deuterium in the run were chosen to produce easily measurable peaks. Geothermal exploration waters contain, in general, far less $D_2O$ so that the isotope ratio mass spectrometer is required to determine m/e 17/m/e 16 ratio in methane.

EXAMPLE II

A break-seal capsule containing 0.1 of water was placed in a 10 cc bomb. After the catalyst was added, the bomb was sealed and evacuated. Next, methane was injected into the bomb until the pressure reached 200 torr. At this point, the break-seal capsule was broken by shaking the bomb.

The bomb was then heated at a desired temperature for a specified time period. The degree of equilibration was measured and a sample was allowed to cool to room temperature. The methane then was introduced into the mass spectrometer through a dry ice trap to remove the water vapor. The m/e 17/m/e 16 ratio was then determined.

This procedure was repeated using samples containing varying concentrations of deuterium, varying type and amount of catalyst. The samples were heated at temperatures ranging from 300° C to 400° C (572° F to 752° F) at pressures of about 400–600 for a time ranging between 30 and 4200 minutes.

The results shown in Table I indicate that the m/e 17/m/e 16 ratios are proportional to the concentration of deuterium in water.

Table I

| % $D_2O$ | Catalyst Amount (1) | Catalyst Type (2) | Temp. C | Time, min. | Equilibration* | m/e 17 / m/e 16 |
|---|---|---|---|---|---|---|
| 1.0 | 90 P | II | 371 | 180 | 62 | 0.024 |
| 2.0 | 1 g | I | 400 | 110 | 66 | 0.053 |
| 0.5 | 1 g | I | 400 | 97 | 63 | 0.013 |
| 1.0 | 1 g | I | 400 | 120 | 66 | 0.027 |
| 2.0 | 1 g | I | 400 | 120 | 60 | 0.048 |
| 0.0 | 1 g | I | 400 | 120 |  | 0.003 |
| 1.0 | 10 P | II | 400 | 120 | 54 | 0.022 |
| 1.0 | 10 P | II | 400 | 120 | 46 | 0.018 |
| 0.5 | 10 P | II | 400 | 60 | 53 | 0.011 |
| 2.0 | 10 P (3) | II | 400 | 30 | 29 | 0.023 |
|  |  |  |  | 232 | 50 | 0.040 |
| 2.0 | 10 P (4) | II | 400 | 55 | 64 | 0.051 |
| 1.0 | 10 P (5) | II | 400 | 115 | 56 | 0.023 |
|  | (3) |  |  | 1015 | 65 | 0.026 |
| 0.5 | 10 P (6) | II | 300 | 60 | 75 | 0.015 |
|  |  |  |  | 960 | 85 | 0.017 |
| 0.5 | 2 g | I | 300 | 3765 | 45 | 0.009 |

(1) P = No. Pellets, g = grams; approximate weight of a pellet = 0.052 grams.
(2) Catalyst I was Raney nickel, and catalyst II is "Calsicat Ni 230 TU 60% Ni on alumina reduced and stabilized."
(3) Same catalyst and sample, heated additional time.
(4) Catalyst from the immediately preceding run was reused in this run; new reactants were added thereto.
(5) Catalyst pretreated to 400° C for 180 min. in hydrogen having pressure of 250 torr.
(6) Catalyst from the immediately preceding run was reused in this run; new reactants were added thereto.
*On a scale 0 = no equilibration, 100 = complete equilibration

We claim:
1. A method for determining a concentration of deuterium in water which comprises the steps of:
   a. equilibrating consecutively at least two water samples having known and varied deuterium concentrations with the same amount of hydrocarbon reagent to allow exchange of hydrogen and deuterium between water and the hydrocarbon reagent until sufficient amount of deuterium migrated to permit the analysis of the mass ratio of isotopes of the equilibrated reagent containing deuterium to those containing hydrogen;
   b. analyzing consecutively the hydrocarbon reagents equilibrated with water samples to determine for each sample the mass isotope ratio of molecules that contain deuterium to those that contain hydrogen;
   c. correlating the isotope mass ratios determined in step (b) with respective known deuterium concentrations of each sample;
   d. reacting water sample of unknown deuterium concentration with the same reagent and under the same conditions as samples in step (a);
   e. establishing by analysis of the reagent equilibrated in step (d) the isotope mass ratio of molecules which contain deuterium to those that contain hydrogen; and
   f. converting the isotope ratio determined in step (e) to deuterium concentration in water using the correlation obtained in step (c).

2. A method as claimed in claim 1 wherein
said hydrocarbon reagent is a saturated hydrocarbon; and
said analyzing step includes the use of isotope ratio mass spectroscopy.

3. A method as claimed in claim 1 wherein
said hydrocarbon reagent is methane;
said equilibrating is conducted in the presence of a catalyst selected from the group consisting of Raney nickel, a reduced and stabilized nickel on alumina catalyst and a nickel-alumina-barium catalyst;
said reacting is carried out under pressure in the range from about 400 to about 600 psia and the temperature in the range from about 572° F (300° C) to about 752° F (400° C) for the time from about 30 to about 4000 minutes; and
said analyzing step includes the use of isotope ratio mass spectroscopy to determine m/e 17/m/e 16 ratio.

4. A method as claimed in claim 3 wherein said catalyst is Raney nickel in the amount of between about 1 gram and about 2 grams per $2.6 \times 10^{-3}$ STP liters of methane; and
said reacting is carried under pressure of 200 torr, temperature between 572° F (300° C) and 752° F (400° C) for a period of about 1 hour.

5. A method as claimed in claim 4 wherein a mole ratio of water to methane prior to the reaction is in the range from about 50 to about 500.

* * * * *